(12) United States Patent
Han et al.

(10) Patent No.: US 6,242,036 B1
(45) Date of Patent: Jun. 5, 2001

(54) CHEESE CURD MADE USING TRANSGLUTAMINASE AND A NON-RENNET PROTEASE

(75) Inventors: Xiao-Qing Han, Glenview, IL (US); Joseph E. Spradlin, Hot Springs, AR (US)

(73) Assignee: Kraft Foods, Inc., Northfield, IL (US)

( * ) Notice: Subject to any disclaimer, the term of this patent is extended or adjusted under 35 U.S.C. 154(b) by 0 days.

(21) Appl. No.: 09/587,305

(22) Filed: Jun. 5, 2000

Related U.S. Application Data

(62) Division of application No. 09/300,136, filed on Apr. 27, 1999, now Pat. No. 6,093,424.

(51) Int. Cl.[7] ................................................ A23C 19/045
(52) U.S. Cl. ............................................................. 426/582
(58) Field of Search ............................... 426/582, 36, 38, 426/40, 42

(56) References Cited

U.S. PATENT DOCUMENTS

| | | | |
|---|---|---|---|
| 3,535,304 | * 10/1970 | Muller et al. | 260/120 |
| 4,205,090 | * 5/1980 | Maubois et al. | 426/40 |
| 5,156,956 | * 10/1992 | Motoki et al. | 435/68.1 |
| 5,205,235 | * 4/1993 | Iacobucci | 435/68.1 |
| 5,356,639 | * 10/1994 | Jameson et al. | 426/40 |
| 5,523,237 | * 6/1996 | Budtz et al. | 435/68.1 |
| 5,629,037 | * 5/1997 | Gaffney | 426/36 |
| 5,681,598 | * 10/1997 | Kuraishi et al. | 426/36 |
| 5,731,183 | * 3/1998 | Kobayashi et al. | 435/193 |
| 6,093,424 | * 7/2000 | Han et al. | 426/42 |

FOREIGN PATENT DOCUMENTS

| | | |
|---|---|---|
| 59-059151 | * 4/1984 | (JP) . |
| 02276541 | * 11/1990 | (JP) . |
| 93/22930 | * 11/1993 | (WO) . |
| 94/21129 | * 9/1994 | (WO) . |
| 94/21130 | * 9/1994 | (WO) . |
| 97/01961 | * 1/1997 | (WO) . |

OTHER PUBLICATIONS

Ernstrom et al., J. Dairy Science 63:2298–234 (1980).*

Banks, J.M. et al., IG (1987). Increasing the yield of Cheddar Cheese by the acidification of milk containing heat–denatured whey protein. Milchwissenschaft 42 (4), pp. 212–215.*

Law, A.J.R. et al., IG [1994]. Denaturation of the whey proteins in heat milk and their incorporation into Cheddar cheese. Milchwisenschaft 49 (2), pp. 63–67.*

Guinee, Timothy P. et al., Composition, Microstructure and Maturation of Semi–Hard Cheeses From High Protein Ultra–filtered Milk Retentates With Different Levels of Denatured Whey Protein, Int. Dairy Journal 5, p. 543–568, 1995.*

Han, Xiao–Qing et al., [1996]. Thermodynamic Compatibility of Substrate Proteins Affects Their Cross–Linking by Transglutaminase. J. Agri. Food Chem. 44 (5) pp. 1211–1217.*

Dybing S. T., et al. [1998], Diary Foods—The Ability of Phosphates or—Carrageenan to Coagulate Whey Proteins and the Possible Uses of Such Coagula in Cheese Manufacture. J. Dairy Sci. 81 (2) pp. 309–317.*

Malin et al. "Chemistry of Structure–function relationships in cheese", Plenum Press, pp. 221–236; 359–365, 1995.*

Fox, P. "Cheese: Chemistry, Physics and Microbiology, vol. 1", Elsevier Appl. Sci. Pub., pp. 71–83, 1987.*

Davies et al. "Advances in the Microbiology and biochemistry of cheese and fermented milk", Elsevier Appl. Sci. Pub., pp. 213–221, 1984.*

\* cited by examiner

*Primary Examiner*—Keith Hendricks
(74) *Attorney, Agent, or Firm*—Fitch, Even, Tabin & Flannery

(57) ABSTRACT

The present invention provides a cheese curd that contains protein products originating from a dairy liquid containing casein and whey protein. In order to obtain the cheese curd, the dairy liquid is acted upon by a transglutaminase and a non-rennet protease, resulting in a substantial proportion of whey protein products being retained in the cheese curd. The invention also discloses a method of making the cheese curd that retains a substantial proportion of whey protein products. This invention further provides a cheese product, such as a soft cheese, a semi-soft cheese, or a hard cheese, that contains protein products originating from a dairy liquid containing casein and whey protein, and a method of making the cheese product.

10 Claims, 1 Drawing Sheet

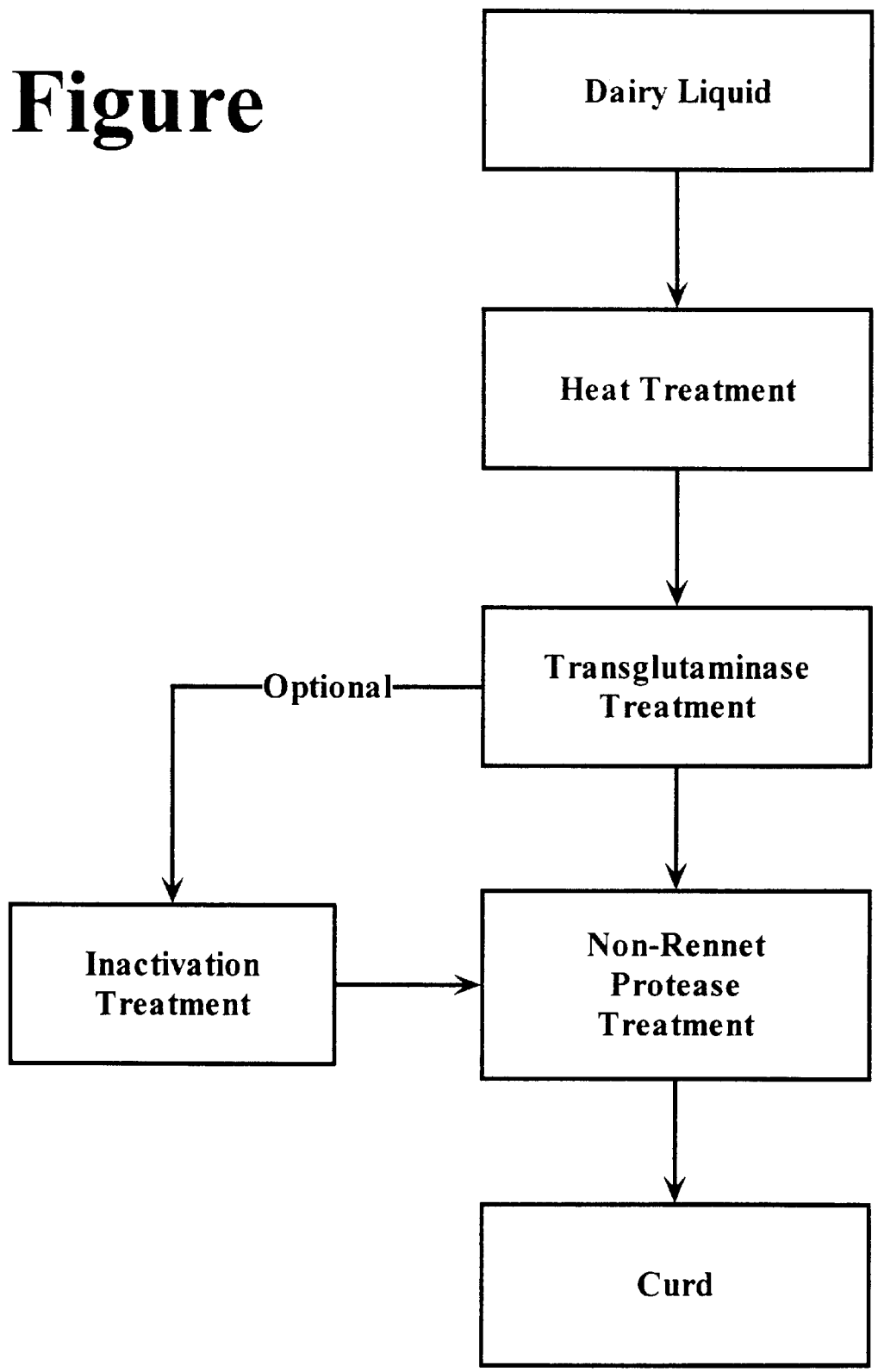

CHEESE CURD MADE USING TRANSGLUTAMINASE AND A NON-RENNET PROTEASE

This is a division, of prior application Ser. No. 09/300, 136, filed Apr. 27, 1999, now U.S. Pat. No. 6,093,424, which is hereby incorporated herein by reference in its entirety.

FIELD OF THE INVENTION

This invention relates to a method that increases the incorporation of whey protein in cheese. The method combines the use of transglutaminase and a non-rennet protease to prepare cheese curd incorporating a significant proportion of whey protein.

BACKGROUND OF THE INVENTION

Cheese compositions are generally prepared from dairy liquids by processes that include treating the liquid with a coagulating or clotting agent. The coagulating agent may be a curding enzyme, an acid, or a suitable bacterial culture or it may include such a culture. The coagulum or curd that results generally incorporates transformed casein, fats including natural butter fat, and flavorings that arise especially when a bacterial culture is used. The curd is usually separated from the whey. The resulting liquid whey generally contains soluble proteins not affected by the coagulation; such proteins are, of course, not incorporated into the coagulum. The inability of whey proteins to be retained in the coagulum is an important factor contributing to a lack of efficiency in production of cheese curds, and to a reduction in overall yield relating to the incorporation of all the protein solids that are present in the starting dairy liquids into resulting cheese curds. These problems have been recognized for many years.

Several methods have been proposed with the objective of recovering whey proteins in cheese products. For example, whey proteins have been concentrated or dried from whey, and then recombined with cheese (see, e.g., Kosikowski, Cheese and Fermented Foods, 2nd ed., Edwards Brothers, Inc., Ann Arbor, Mich., 1977, pp. 451–458). Unfortunately the whey recovered from such procedures does not have the appropriate physical and chemical properties conducive to making good quality natural cheeses or process cheeses.

An alternative approach has been to coprecipitate whey proteins with casein, as disclosed, for example, in U.S. Pat. No. 3,535,304. Again, however, the final product of this process lacks the proper attributes for making processed and imitation cheeses.

A further attempt to incorporate whey proteins into cheese products has employed ultrafiltration of milk to concentrate all the components, such as the casein, the whey protein, and the butterfat, that do not permeate the ultrafiltration membrane. When such a composition is coagulated by contact with an acid or rennet, a curd forms. This curd, however, loses considerable quantities of the whey protein during compaction. An example of such a process is provided in U.S. Pat. No. 4,205,090 wherein the milk is concentrated to about one-fifth of its original volume. The resulting curd could only be used to provide soft cheeses such as Camembert or Roblechon. Hard cheeses, such as cheddar, Colby, and the like, could not be prepared using this product.

Ernstrom et al. (J. Dairy Science 63:2298–234 (1980)) described a process in which milk is concentrated to about 20% of the original volume by ultrafiltration, diafiltration, and evaporation. The resulting composition is then inoculated with a cheese starter to ferment the lactose and form a cheese base. The cheese base can be used to replace natural cheese components of process cheese. This process does not employ any renneting step to prepare a cheese curd.

Food processing methods employing transglutaminases have also been disclosed in recent years. For example, Japanese Patent 59059151 discloses treating an emulsion containing proteins, oils or fats, and water with transglutaminase to produce a gelatinous, crosslinked gel. Japanese Patent 02276541 discloses a food protein with a fiber texture having heat-resistance. The fiber texture is developed by treatment of a protein hydrogel with a transglutaminase in the presence of calcium ion to induce crosslinking of the surface of a fiber bundle. Japanese Patent 2131539 used transglutaminase to work on a fused cheese product containing milk solids to product a cheese food having a texture similar to boiled fish paste.

U.S. Pat. No. 5,156,956 discloses a transglutaminase purified from strains of the genus Streptoverticillium, as well as its chemical, physical, and enzymatic properties. This transglutaminase catalyzes formation of protein gelation products from protein solutions to produce conventional gel foodstuffs such as yoghurt, jelly, cheese, gel cosmetics, and the like. This method did not use transglutaminase and enzymatic clotting agents to produce cheese.

U.S. Pat. No. 5,356,639 discloses a process for the production of a fermented concentrate from milk, including whole milk, skim milk, and milk with added milk components. The concentrate could be used to make cheese. The process includes the steps of (1) selectively concentrating milk; (2) increasing the ionic strength of the concentrate to maintain the milk in a the liquid phase (coagulum formation is prevented both during and after fermentation); (3) fermenting the concentrate with lactic acid producing bacteria; and (4) removing water from the fermented liquid concentrate. The final product includes substantially all of the whey proteins originally present in the milk.

U.S. Pat. No. 5,681,598 describes a process for producing cheese with transglutaminase. The process includes (1) adding a transglutaminase to a milk or milk protein solution, (2) heat-treating the mixture, (3) adding a milk clotting enzyme for a fixed time, and (4) recovering a cheese. This process provides a large amount of cheese curd compared to conventional methods. Additionally, processes in which conventional cheese fermentation occurs first and transglutaminase treatment occurs subsequently, as well as simultaneous treatments, are disclosed. The milk clotting enzyme is preferably an animal rennet. Increases in total weight, but not in dry weight, of the curd when transglutaminase is used were observed.

U.S. Pat. No. 5,731,183 discloses a transglutaminase purified from strains of *Bacillus subtilis*, having particular physical and enzymatic characteristics, and a method for producing protein, peptide, or non-protein amino acid polymers that are cross-linked via their glutamine and lysine residues to form intermolecular or intramolecular conjugates. The transglutaminase may be used to produce crosslinked protein polymers that can be used in a variety of food substances including cheese. This reference differs from the instant disclosure in characterizing a bacterial transglutaminase while not disclosing process steps utilizing transglutaminase and clotting agents that are involved in producing cheese.

Banks et al. (*Milchwissenschaft* 42:212–215 (1987)) disclose that heating milk at temperatures from 95° C. to 140° C. and then acidifying permits a modest increase in protein content in the cheese upon Cheddar production. Unfortunately, the resulting cheese developed a bitter off-flavor in this process. Law et al. (*Milchwissenschaft* 49:63–37 (1994)) report that heat treatment of milk prior to cheddaring results in reduction of proteins in whey and/or in acid filtrates of the milk.

Han et al. (*J. Agri. Food Chem.* 44:1211–1217 (1996)) examined the activity of transglutaminase in forming heterologous dimers and trimers. It was found that β-casein forms homopolymers whereas β-lactoglobulin does not. In heterologous mixtures, transglutaminase was shown to catalyze dimer formation between α-lactalbumin and β-casein but not between β-casein and β-lactoglobulin. Han et al. do not discuss any aspect of cheese production.

U.S. Pat. No. 5,523,237 discloses a plastein material which is defined as one made by reversing the activity of a protease enzyme (e.g., a serine protease) acting on proteinaceous material. The proteinaceous substrate is present at a concentration of 5–50%, and is preferably whey, casein, or soy protein. The enzyme preparation is substantially free of subtilisin A activity, and is specific for glutamic acid and aspartic acid residues. This protease is obtained from *Bacillus licheniformis* and is designated SP 446; its proteolytic activity is characterized in considerable detail. The viscosity of whey protein containing solutions is shown to increase as a result of the action of the enzyme.

International patent WO 93/22930 discloses treating milk with a transglutaminase (preferably mammalian activated Factor XIII) and then with an enzyme having milk clotting activity to provide a milk-like product. According to this publication, the product has microparticulated protein that has been aggregated by means of the enzyme with milk clotting activity, and has mouthfeel that resembles a fat emulsion. Preferably the milk clotting enzyme is a cheese rennet enzyme. This method, like that of U.S. Pat. No. 5,356,639, does not provide a cheese curd.

International patent WO 94/21129 discloses a process for forming an acidified edible gel from milk. Transglutaminase is added to milk or a milk-like product, the pH is adjusted to 4.8 to 5.8, and the resulting composition is exposed to a heat treatment. The resulting edible gel is reported to have a pleasant consistency and mouthfeel. International patent WO 94/21130 discloses a similar process for forming an edible gel from milk. Transglutaminase is added to milk or a milk-like product, rennet is then added, and the resulting composition is exposed to a heat treatment. Only a single phase gel (rather than separate curd and whey) was obtained. This gel is reported to have satisfactory organoleptic properties.

International patent WO 97/01961 discloses a process for making cheese which retains proteins in the cheese. The milk is incubated with transglutaminase, followed by a treatment with a rennet to cause clotting and formation of a coagulate. After separating the whey from the coagulate, the coagulate is used to make cheese. The protein to be maintained in the cheese, as set forth in the description, relates to casein macropeptides that result from the action of the rennet, and that diffuse into the whey. This process differs from the instantly claimed invention in a number of ways. The process disclosed in this patent relates to the retention of casein macropeptides, rather than whey protein, in the cheese curd. Moreover, there is no requirement for an initial heating step, and the rennet employed in WO 97/01961 is a conventional mammalian rennet.

Dybing et al. (*J. Dairy Sci.* 81:309–317 (1998)) postulated incorporating whey protein into cheese curd by concentrating the components, coagulating whey proteins using a variety of agents, and rennetting a composition containing the coagulated whey protein and concentrated milk components. It was found, however, that none of the methods attempted succeeded in producing whey protein coagula that were recovered as cheese.

Guinee et al. (*Int. Dairy journal* 5:543–568 (1995)) reviewed the state of the art relating to incorporation of whey protein into cheese. High-heat treatment of milk impairs rennet coagulation, curd syneresis, curd structure and texture, as well as functional properties such as meltability and stretchability. Guinee et al. discuss physical and chemical factors that may be responsible for these effects. In heat treatments that denature whey protein in milk compositions, they found that, in semi-hard cheeses that result from curding such treated compositions, the curd has higher whey protein levels, but also higher moisture level, lower pH value, poorer curd fusion and lower yield (fracture) values during ripening.

In spite of many attempts documented over almost three decades of effort, there remains a need for a cheese curd with significantly increased incorporation of whey protein into the curd without significant reduction of organoleptic properties, and for a method that significantly increases the incorporation of whey protein into cheese curd without adversely affecting the organoleptic and other properties of the resulting cheese. There further remains a need for cheese products prepared from dairy liquids that have significantly increased retention of the whey protein, and for a method of making cheese products that significantly increases the incorporation of whey protein into the cheeses. Additionally there remains a need for enhancing the yield and efficiency of making cheese by significantly increasing the incorporation of whey protein into cheese products. The present invention satisfies these long-felt needs and discloses methods and cheese compositions that address them.

SUMMARY OF THE INVENTION

The present invention provides a cheese curd that contains protein products originating from a dairy liquid containing casein and whey protein. In order to obtain the cheese curd, the dairy liquid is acted upon by a transglutaminase and a non-rennet protease, resulting in a substantial proportion of whey protein products being retained in the cheese curd. The invention also provides a method of making such cheese curd. The method employed to prepare the cheese curd includes the sequential steps of (i) heating the dairy liquid to a temperature of about 55 to about 90° C. for at least about 2 minutes;

(ii) cooling the heat treated dairy liquid to a temperature of about 30 to about 65° C.;

(iii) contacting the cooled dairy liquid with a transglutaminase to provide a modified dairy liquid;

(iv) contacting the modified dairy liquid with a non-rennet protease to form cheese curd and whey liquid; and (v) separating the cheese curd from the whey liquid.

This invention also provides cheese products (soft, semi-soft, or hard) containing protein products originating from a dairy liquid containing casein and whey protein. The use of transglutaminase and a non-rennet protease allows retention of a substantial proportion of whey protein products in the cheese curd. The invention also provides a method of making the cheese product that retains a substantial proportion of whey protein products.

The transglutaminase may be isolated from various sources, including, for example, bacteria, fungi, molds, fish, or mammals. The transglutaminase is preferably isolated from a microbial source, most preferably from the genus Streptoverticillium. The non-rennet protease is a bacterial protease, a plant protease, a fish intestinal protease, or an animal protease other than mammalian rennet. Advantageously the non-rennet protease is a bacterial protease, such as the protease Novo SP 446 isolated from *Bacillus licheniformis*, and the microbial protease Coralase PN-L produced by *Aspergillus sojae* (Rohm GmbH, Germany). The protease Novo SP 446 is especially preferred. The temperature used in the heating step is preferably between about 65 and about 85° C., and most preferably between about 75 and about 77° C. The cheese curd resulting from this method may be used to provide soft, semi-soft, or hard cheeses.

BRIEF DESCRIPTION OF THE DRAWING

The FIGURE provides a schematic flow chart of the present process for making a cheese curd containing a substantial proportion of whey protein products.

DETAILED DESCRIPTION OF THE INVENTION

The present invention provides a cheese curd from dairy liquids containing casein and whey protein. The curd composition contains protein products provided by the action of, first, a heat treatment, then a transglutaminase treatment, and, subsequently, a treatment using a non-rennet protease; these treatment steps appear to act directly on the proteins in the dairy liquid. The resulting cheese curd retains a substantial proportion of whey protein products. This curd can be further processed to provide cheese products including soft, semi-soft, or hard cheeses. The invention also provides methods for making the cheese curd and the cheese product. The retention of the whey protein products in the cheese curd, and in the cheese products, provides a significant enhancement in the efficiency of utilization of the total protein in the starting raw material (i.e., the dairy liquid), while retaining desired organoleptic properties. This property also provides a higher yield of edible, nutritive solids in the products than is found in cheeses currently available.

The FIGURE provides a general schematic flow chart for the process of this invention leading to the production of a curd which retains a substantial proportion of the whey proteins. The starting material of the present invention is a dairy liquid that includes casein and whey protein. As used herein, "dairy liquid" relates to milk, milk products obtained by fractionating raw milk to provide a liquid fraction, or a solid milk fraction that is reconstituted to a liquid. For example, the milk may be treated to remove some or all of the butterfat, providing low fat milk or skim milk, respectively. Furthermore, whole milk, low fat milk, or skim milk may be concentrated by methods such as evaporation and/or ultrafiltration (with or without diafiltration) and the like. Evaporation provides dairy liquids containing a higher concentration of all the nonvolatile components, whereas ultrafiltration provides dairy liquids with a higher concentration of the components that are nonpermeable to the ultrafiltration membrane. In any case, the dairy proteins including casein and whey protein are included among the retained solids, such that their concentrations in the resulting liquids are increased. Furthermore any of the above dairy liquids may be evaporated to dryness, providing milk solids originating from whole milk, low fat milk, or skim milk. Any of these solids may be reconstituted by the addition of water or a suitable aqueous composition including milk or a milk fraction. Reconstitution of dry milks thus provides dairy liquids that in general may have a broad range of final concentrations of the component proteins, butterfat, and other components. All the above liquids are included in the designation of "dairy liquids" as used herein.

The dairy liquids employed in the present invention may originate from any lactating livestock animal whose milk is useful as a source of human food. Such livestock animals include, by way of nonlimiting example, cows, buffalo, other ruminants, goats, sheep, and the like. Generally, however, cows' milk is the preferred dairy liquid used in the practice of the invention.

As used herein, "casein" relates to any, or all, of the phosphoproteins in milk. An important characteristic of casein is that it forms micelles in naturally occurring milk and in the dairy liquids employed in the present invention, and that clotting a dairy liquid containing casein by any suitable means provides a coagulated curd phase and a liquid whey phase that are separable from one another. Many casein components have been identified, including, but not limited to, $\alpha$-casein (including $\alpha_{s1}$-casein and $\alpha_{s2}$-casein, $\beta$-casein, $\kappa$-casein, their genetic variants, and mixtures thereof.

As used herein, "whey protein" relates to the proteins contained in a dairy liquid obtained as a supernatant of the curd when milk or a dairy liquid containing milk components are curded to produce a cheese-making curd as a semisolid. Whey protein is generally understood to include principally the globular proteins $\beta$-lactoglobulin and $\alpha$-lactalbumin. It may also include significantly lower concentrations of immunoglobulin and other globulins.

Transglutaminases are enzymes which catalyze the transfer of the $\gamma$-carboxamide group of a glutaminyl residue in a protein or peptide to the $\epsilon$-amino of a lysyl residue of the same or a different protein or peptide, thereby forming a $\gamma$-carboxyl-$\epsilon$-amino crosslink. Transglutaminases have a broad occurrence in living systems, and may be obtained, for example, from microorganisms such as those belonging to the genus Streptoverticillium, Bacillus subtilis, various Actinomycetes and Myxomycetes, or from plants, fish species, and mammalian sources including pig liver and the blood clotting protein activated Factor XIII. In general, transglutaminases from animal sources require calcium ions for activity. Recombinant forms of transglutaminase enzymes may be obtained by genetic engineering methods as heterologous proteins produced in bacterial, yeast, and insect or mammalian cell culture systems. The principal requirement of any transglutaminase employed in the instant invention is that it have the crosslinking activity discussed above. Any enzyme having transglutaminase activity may be employed in the methods of the present invention. In a preferred embodiment, the transglutaminase is obtained from the genus Streptoverticillium.

Transglutaminase activity may be determined using known procedures. One such colorimetric procedure uses benzyloxycarbonyl-L-glutaminyl-glycine and hydroxylamine to form a $\gamma$-carboxyl-hydroxamic acid if transglutaminase is present. An iron complex of the hydroxamic acid can be formed in the presence of ferric chloride and trichloroacetic acid. Using the absorbance at 525 nm with appropriate standards, the activity of enzyme present may be determined. See, for example, U.S. Pat. No. 5,681,598.

Rennet is a generic term used in the field of dairy science and in the field of cheese making, to designate an activity obtained from the lining of the stomachs of immature mammals that consume maternal milk. The natural function of rennet is to initiate the digestion of the milk in order to provide the nutrition contained in the milk protein to the young mammal. In cheese making, rennet is used to clot the dairy liquids, thereby forming cheese curd and whey. The term "renneting" relates to the process of treating a dairy liquid with a rennet to provide a cheese curd and whey. Synonyms for "renneting" include "curding", "clotting", and "setting". As used in contemporary dairy science, "rennet" connotes-the enzyme earlier called "rennin" and now termed "chymosin". Chymosin is a member of the family of proteases known as aspartyl endopeptidases.

The activity of chymosin on dairy liquids includes at least the proteolytic cleavage of the peptide bond between the phenylalanyl residue that occurs at about position numbered 105 and the methionine that occurs at about position numbered 106 in $\kappa$-casein to release a soluble macropeptide and induce the coagulation of the remainder of the molecule, termed para-$\kappa$-casein, with all the components of the casein micelles. Common natural sources of chymosin include, but are not limited to, the stomachs of calves, buffalo, other ruminants, kid goats, lambs, piglets, and the like. Furthermore, various natural chymosins and genetically engineered chymosin mutant proteins are available as the recombinant protein products, obtained as a result of introducing genes encoding these proteins as heterologous genes in order to make the gene products in suitable host organisms. Chymosin is the activated form produced when the proenzyme prochymosin is activated. Prochymosin likewise may be a recombinant product, and may be a genetically engineered mutant protein which upon activation provides renneting activity. As used herein, all such chymosins having renneting activity, and prochymosins activatable to such chymosins, are included in the term "rennet".

Many other non-rennet enzymes have coagulating activity. Nonlimiting examples include other aspartyl proteases such as various pepsins, and a large number of proteases from nonmammalian sources, including plants, microorganisms, and marine fishes. As used herein, a "non-rennet protease" relates to any such protease having milk-clotting activity that is not a rennet as defined herein. Furthermore, various natural non-rennet proteases, as well as genetically engineered mutant proteins derived from such natural proteases and having the corresponding protease activity, are available as recombinant protein products, obtained upon introducing genes encoding these proteins as heterologous genes into suitable host organisms to produce the protein products. As used herein, all such recombinant non-rennet proteases having milk-clotting activity are included in the term "non-rennet protease".

Among the non-rennet proteases that may be used in the present invention are the bacterial protease obtained from *Bacillus licheniformis* and designated SP 446 (Novo Nordisk), the bacterial protease from *Bacillus thermoproteolyticus*, the microbial protease Coralase PN-L produced by *Aspergillus sojae* (Rohm GmbH, Germany), a plant protease such as papain, animal proteases such as a protease from the intestines of fishes. In a preferred embodiment, the protease employed is SP 446. The proteases that may be used in the process of the invention include proteases that are capable of functioning at relatively high temperature. Thus, the temperature range in which the coagulation may be carried out is from about 20 to about 75° C., and more preferably is in the range from about 35 to about 65° C. The pH may be in the range from about 5.5 to about 9.0, and more preferably may be in the range from about 6.0 to about 8.0. The duration of treatment is a very important aspect of the invention, and is related in a complex way to the specific conditions of temperature and pH chosen from the broad ranges established herein. In general, as the temperature is increased (as long as the transglutaminase is not inactivated), and as the pH approaches the pH optimum of the transglutaminase, the activity of the enzyme is expected to increase, and correspondingly the duration of treatment may be expected to decrease. For example, for transglutaminase from Streptoverticillium, the pH optimum as about 6 to 7. It also is related to the actual clotting activity to which a given dairy liquid already treated with transglutaminase is exposed. In general, the time of digestion may vary from about 5 to about 120 minutes or longer. It is preferred to specify digestion conditions such that the digestion time is kept to a convenient duration, such as about 30 to about 60 minutes. The duration of treatment under a given set of conditions may be readily determined by a worker of skill in the field of cheese making by optimizing the incorporation of whey protein digestion products into cheese curd using those conditions. The coagulation procedure provided by the present invention unexpectedly yields a cheese curd that retains a significant proportion of the whey protein originally present in the dairy liquid as a whey protein product.

In the methods for making a cheese curd, and for making a cheese product, of the present invention, a first important step is the heating of the dairy liquid at a temperature between about 55 and about 90° C. Of course, this temperature is limited at the upper end of its range in order to avoid, for example, detrimental occurrences such as foaming or precipitation of the proteins in the liquid, or development of excessive vapor pressure if the heating is done in a closed system, or the like. In preferred embodiments of the methods, the temperature is between about 65 and about 85° C., and in a more preferred embodiment, the temperature is between about 75 and about 77° C. This heating step relates to a sustained heating for an extended period of time sufficient to alter the state of the proteins in the dairy liquid in such a way as to permit the final curd or cheese product to be successfully prepared. Thus, this heating step is continued for at least 2 minutes, preferably for about 10 to about 20 minutes. Without wishing to be limited by theory, it is believed that this heat treatment effects a partial denaturation or unfolding of the proteins in the dairy liquid. For this reason, the heating step is to be distinguished from a transient heating, such as a pasteurization heating, which in general may be carried out at a temperature of about 72° C. to about 120° C., and may last for only a brief time interval (generally from about 2 sec to about 90 sec); such a pasteurization step should not significantly effect the structure of the dairy liquid. As shown in Example 2, this heating step is required to provide the cheese curd and the cheese product of the present invention. Following the heating step, the dairy liquid is cooled to a temperature suitable for the introduction of a transglutaminase. Generally, such cooling is to a temperature below about 65° C., and preferably between about 30° C. and about 60° C.

As shown in the FIGURE, the next step involves treatment of the heat treated and cooled dairy liquid with a transglutaminase. An amount having sufficient transglutaminase activity to modify the dairy liquid as described herein is required. The known enzymatic activity of transglutaminase involves the catalytic transfer of the γ-carboxamide group of a glutaminyl residue in a protein or peptide to the ε-amino of a lysyl residue of the same or a different protein or peptide. Without wishing to be bound by theory, if such reactions were to occur in the dairy liquid, glutaminyl-lysyl side chain-side chain crosslinks would form between the protein components present, including crosslinks among and between any of the caseins and any of the whey proteins. The modified dairy liquid produced by the action of the transglutaminase may include protein molecules crosslinked in this fashion. Generally, the treatment with transglutaminase is continued for about 10 to about 300 minutes, and preferably for about 40 to about 120 minutes. After modifying the dairy liquid with transglutaminase, the transglutaminase may optionally be inactivated by, for example, a brief exposure of the modified dairy liquid to an elevated temperature (generally about 70° C. to about 80° C. for about 5 to about 10 minutes) sufficient to achieve inactivation. Such inactivation is not, however, required.

A significant further step in the present methods is treatment of the modified dairy liquid with a non-rennet protease. The non-rennet protease may be a bacterial protease or it may be an animal protease other than a rennet as defined herein. In important embodiments of the methods, the non-rennet protease may be a bacterial protease such as the glutamyl endopeptidase produced by *Bacillus licheniformis* (SP 446) obtained from Novo Nordisk, a microbial protease such as Coralase PN-L produced by *Aspergillus sojae*, obtained from Rohm GmbH, Germany, a plant protease such as papain, or a protease from fish intestines. In a more important embodiment, the non-rennet protease is Novo SP 446. The properties and optimal conditions for using Novo SP 446 are set forth, for example, in U.S. Pat. No. 5,523,237. The non-rennet protease brings about coagulation of the modified dairy liquid to form a cheese curd and the corresponding whey liquid. These components resolve into separable phases which may be separated from each other by suitable conventional procedures such as centrifugation, filtration, application of pressure, or the like.

As the worker skilled in cheese making and dairy science appreciates, the dairy liquid is transformed, according to the methods of the invention, by virtue of the treatment at an elevated temperature and the activities of the transglutaminase and the non-rennet protease. Thus, although the starting dairy liquid contains dairy proteins whose properties and structures are well known to the skilled artisan, the products obtained by the sequential action of these activities are not clearly understood. Thus both the curd and the whey liquid may contain a large variety of protein and peptide components, as well as proteins of the starting dairy liquid that may not have been altered by the enzymatic activities applied in the process. For this reason, the terms "protein products originating from a dairy composition comprising casein and whey protein", "whey protein products", and equivalent phrases, are used herein to designate the products, currently uncharacterized, that may constitute the cheese curd and that may be present in the whey liquid. A substantial proportion of the original whey protein, present as whey protein products, is retained in the cheese curd of the invention rather than being found in the whey liquid. This result is heretofore uncharacterized in the field of cheese making and is therefore surprising to a worker of skill in the art.

The cheese curd retaining a substantial proportion of whey protein products may be processed further to make a large variety of cheese products, including, for example, soft, semi-soft, and/or hard cheeses. Such processing contributes factors of flavor, consistency, organoleptic properties, and the like, and is accomplished by processes such as fermentation with selected cheese-making microorganisms, subjecting the curd to additional enzymatic activities, and the like, in ways that are known to a person skilled in dairy science and cheese making.

The following examples are intended to illustrate the invention and not to limit it. The leading example (i.e., Reference Example) is provided for comparative purposes only. Unless indicated otherwise, all percentages are by weight.

REFERENCE EXAMPLE

Lack of Curd Formation Using Transglutaminase and Rennet

Skim milk was treated using various sequences involving the order of transglutaminase treatment and conventional renneting. This permitted assessing whether use of transglutaminase as a first step in a conventional renneting process could be used to prepare cheese curd. A simple cutoff criterion (i.e., absence of milk clotting by 60 min) was used to determine whether curd formation occurred. The results of these experiments are shown in Table 1.

TABLE 1

Effect of transglutaminase and rennet on curd formation

| No. | First Step | Second Step | Third Step | Result |
|---|---|---|---|---|
| 1 | Heat[a] | Transglutaminase[b] | Rennet[c] | No clot formed |
| 2 | None[d] | Transglutaminase[b] | Rennet[c] | No clot formed |
| 3 | Heat[a] | Rennet | Transglutaminase[b] | Curd formed |

TABLE 1-continued

Effect of transglutaminase and rennet on curd formation

| No. | First Step | Second Step | Third Step | Result |
|---|---|---|---|---|
| 4 | Heat[a] | Heat Inactivated Transglutaminase[b] | Rennet | Curd formed |

[a]63° C. for 30 minutes.
[b]50° C. for 35 minutes (samples 1, 3, and 4) or 30 minutes (Sample 2).
[c]Chymosin at 31° C. as used for cheddar cheese processing.
[d]Raised directly to 50° C. in order to add transglutaminase.

The conditions used in sample 1 were selected to enhance transglutaminase-catalyzed crosslinking of milk proteins. Incubation at 50° C. for this step provides for rapid crosslinking. The absence of clot formation suggests that crosslinking of milk protein by transglutaminase and subsequent renneting are incompatible in a process intended to provide cheese curd. Sample 4 used transglutaminase inactivated by heat treatment before being added to the milk; inactivated transglutaminase had no inhibitory effect on curd formation. In Sample 3, the reversal of the order of treatments with rennet and transglutaminase did not affect curd formation. The preheating step, in which the milk is incubated at an elevated temperature, is also not commonly applied in conventional renneting processes. Sample 2 indicates that the milk does not clot even if there is no heat treatment prior to the enzyme treatments. Samples 3 and 4 show that even when the preheating step was applied, curd formation could proceed unhindered. Therefore, the preheating step used in Sample 1 cannot be the reason that clot formation does not occur. Thus it appears that the crosslinking activity of transglutaminase, applied prior to conventional renneting, interferes with the rennet-catalyzed clotting process, and prevents curd formation.

Example 1

Preparation of Cheese Curds Treated with Transqlutaminase and Non-rennet Protease.

Samples of skim milk (about 40 mL) with a pH of about 6.6 were incubated at 32° C. for 20 minutes. The samples were supplemented with 62 µL of a 1:25 dilution of Cal-SOl™ (45% $CaCl_2$ from Chr. Hansen, Milwaukee, Wis.), and with 0.12 g glucono-delta-lactone, and pre-incubated at 55° C. for 5 minutes. The samples were then incubated at 75° C. for 10, 20, or 30 minutes, and cooled to about 55° C. Aliquots (either 2.0 mL or 4.0 mL) of a 20% solution of transglutaminase (Ajinomoto TG-TI, Teaneck, N.J., containing 100 units of activity per gram enzyme, where 1 unit is defined as the amount of enzyme that catalyzes the formation of 1 micromole hydroxamate per minute under the conditions of assay (Folk, et al., J. Biol. Chem. 240:2951 (1965))) were added, and the samples were incubated at 55° C. for 30 minutes. Novo SP 446 protease (3.0 µL; Novo Nordisk, Franklinton, N.C.) solution (containing 1.28 units/mL, where units are defined as the amount of enzyme that liberates the equivalent of one micromole of tyrosine per minute under the conditions of the assay) were added. The samples were further incubated at 55° C. for 50 minutes. The resulting curd was cut in situ, and incubated at the same temperature for 10 minutes. In order to measure the content of whey protein products in the curd, the curded preparation was centrifuged at 1,500 rpm for 10 minutes at 25° C., the whey was decanted and both whey and curd weighed. The protein content in the whey was determined by Kjeldahl assay, and the whey protein product retained in the curd was obtained by difference from the control. The results (average value based on three experiments) are presented in Table 2.

TABLE 2

Effect of transglutaminase activity and incubation time on incorporation of whey protein product into cheese curd.

| Transglutaminase (μL) | Incubation Time, min | Wet curd (g) | Protein Product in Whey (g) | Protein Product in Curd (g) | Protein Product Retained in Curd (%) |
|---|---|---|---|---|---|
| 0[a] | 0 | 5.85 | 0.293 | (0)[a] | (0)[a] |
| 2.0 | 10 | 12.1 | 0.229 | 0.064 | 21.8 |
| 2.0 | 20 | 11.5 | 0.216 | 0.077 | 26.3 |
| 2.0 | 30 | 11.09 | 0.208 | 0.085 | 29.0 |
| 4.0 | 10 | 13.86 | 0.215 | 0.078 | 26.6 |
| 4.0 | 20 | 13.17 | 0.207 | 0.085 | 29.0 |
| 4.0 | 30 | 12.86 | 0.197 | 0.096 | 32.8 |

[a]Defined as zero.

In Table 2, the control provides the normal amount of whey protein product from a conventional cheddaring process; the amount of curd in the control was assigned a value of zero and all other measurements were made relative to the control. As shown in Table 2, more whey protein product is retained in the cheese curd formed using SP 446 as the incubation time and the transglutaminase activity is increased.

These experiments demonstrate that the action of a non-rennet protease, when applied after treatment with a transglutaminase, provides a cheese curd that retains a significant proportion of whey protein products. The fact that this curd is obtained by the successive application of transglutaminase and a non-rennet protease contrasts sharply with the absence of curd formation found when transglutaminase and a rennet are used (see the Reference Example). Therefore the production of cheese curd by the inventive process and the retention of whey protein products in the resulting curd, which is obtained from the use of a transglutaminase, and a non-rennet protease, is unknown in the art of cheese making and dairy science.

Example 2

Effects of Heat, Transglutaminase and Non-rennet Protease on Incorporation of Whey Protein Products into Cheese Curd Skim milk samples (40 mL) having a pH of about 6.6 were incubated at 32° C. for 20 minutes. The samples were supplemented with 62 μL of a 1:25 dilution of Cal-Sol™ (45% $CaC_2$ from Chr. Hansen), and with 0.12 g glucono-delta-lactone, and then pre-incubated at 55° C. for 5 minutes. The samples were incubated at 75° C. for 10, 20, or 30 minutes, and cooled. Aliquots of 4.0 mL of a 20% solution of transglutaminase (Ajinomoto, 100 units per gram enzyme) were added to experimental samples. No transglutaminase was added to control samples. All samples were incubated at 55° C. for 30 minutes. Then 3.0 μL of Novo SP 446 protease (Novo Nordisk) solution (containing 1.28 units/mL) were added to experimental samples and certain controls, and 6.0 μL of rennet (Chr. Hansen, Milwaukee, Wis.; containing 555 International Milk Clotting Units (IMCU) of activity, where 1 IMCU is the amount of enzyme that clots 10 mL of reconstituted skim milk in 100 s at 32° C.) were added to the remaining control samples. The samples were then incubated at 55° C. for 50 minutes. The resulting curd was cut in situ, and incubated at the same temperature for 10 min. Analysis of the content of whey protein products in the curd, was done as in Example 1. The results (average based on three samples) are presented in Table 3.

TABLE 3

Effect of enzymes and incubation time on incorporation of whey protein product into cheese curd.

| Sample | Incubation Time at 75° C. (min) | Transglutaminase | Novo SP 446 | Rennet | Protein Product in Whey (g/dL) | Protein Product Retained in Curd (%) |
|---|---|---|---|---|---|---|
| 1 | 0[a] | − | − | + | 0.815 | (0)[b] |
| 2 | 10 | − | − | + | 0.728 | 10.7 |
| 3 | 30 | − | − | + | 0.708 | 13.4 |
| 4 | 10 | − | + | − | 0.839 | −3.0 |
| 5 | 30 | − | + | − | 0.774 | 5.1 |
| 6 | 0 | + | + | − | 0.796 | 2.3 |
| 7 | 10 | + | + | − | 0.706 | 13.4 |
| 8 | 30 | + | + | − | 0.616 | 24.4 |

[a]Control: Sample processed under standard conditions for cheddar cheese.
[b]Defined as zero.

Sample 1 in Table 3 establishes a control level of protein products in whey liquid based on a conventional cheddaring process. Samples 2 and 3 provide controls under the conditions of a method of the invention, but in which no transglutaminase is used, and in which the dairy liquid is clotted using rennet, respectively. It is seen that a modest amount of whey protein product is retained in the curd.

When only non-rennet protease is applied (Samples 4 and 5), virtually no protein products are retained.

Inventive samples 6–8 of Table 3 use both transglutaminase and non-rennet protease treatment steps. Incubation for 30 minutes at 75° C. (Sample 8) provides a substantial proportion of whey protein product in the cheese curd. It is also seen, however, teiat in the absence of the incubation step (Sample 6), essentially no protein product is incorporated into the curd. This experiment, therefore, establishes that an important inventive aspect of the present method is the incubation at an elevated temperature. This incubation step incorporated into the present method is uncharacterized in the field of cheese making and dairy science. It is therefore an unexpected feature of the instantly claimed invention.

Example 3

Effects of the Length of Heat Treatment on Incorporation of Whey Protein Products into Cheese Curd Experiments were conducted as described in Example 2, except that the incubation temperature was raised to 77° C. No control experiments investigating the effect of transglutaminase alone, or of SP 446 alone, were carried out in this Example. The results (average values based on three runs) are presented in Table 4.

TABLE 4

Effect of incubation time on incorporation of whey protein product into cheese curd.

| Sample | Incubation Time at 77° C. (min) | Transglutaminase | Novo SP 446 | Rennet | Protein Product in Whey (g/dL) | Protein Product Retained in Curd (%) |
|---|---|---|---|---|---|---|
| 1[a] | 0 | − | − | + | 0.865 | (0)[b] |
| 2 | 0 | + | + | − | 0.752 | 9.8 |
| 3 | 10 | + | + | − | 0.692 | 16.9 |
| 4 | 20 | + | + | − | 0.623 | 25.2 |
| 5 | 30 | + | + | − | 0.526 | 36.9 |

[a]Control: Sample processed under standard conditions for cheddar cheese.
[b]Defined as zero.

The results in Table 4 corroborate the results presented in the last three lines of Table 3. It is shown that incubation at an elevated temperature is required for the incorporation of substantial proportions of whey protein product into cheese curd. This result is unknown in the field and therefore unexpected by the skilled artisan.

Example 4

Effects of the Amount of Transglutaminase Activity on Incorporation of Whey Protein Products into Cheese Curd Experiments were conducted similar to those of Examples 2 and 3. The amount of transglutaminase activity was varied by adding from 0.1 g to 1.5 g of transglutaminase (about 0.25% to about 3.5% of the total sample). No control experiments investigating the effect of transglutaminase alone, or of SP 446 alone, were carried out in this Example. The results (average based on three runs) are presented in Table 5.

TABLE 5

Effect of enzyme activity on incorporation of whey protein product into cheese curd.

| Sample | Incubation Time at 77° C. (min) | Transglutaminase | Novo SP 446 | Rennet | Protein Product in Whey (g/dL) | Protein Product Retained in Curd (%) |
|---|---|---|---|---|---|---|
| 1[a] | 0 | 0.0 | − | + | 0.865 | (0)[2] |
| 2 | 20 | 0.1 | + | − | 0.698 | 16.3 |
| 3 | 20 | 0.2 | + | − | 0.653 | 21.6 |
| 4 | 20 | 0.5 | + | − | 0.621 | 25.5 |

TABLE 5-continued

Effect of enzyme activity on incorporation of whey protein product into cheese curd.

| Sample | Incubation Time at 77° C. (min) | Transglutaminase | Novo SP 446 | Rennet | Protein Product in Whey (g/dL) | Protein Product Retained in Curd (%) |
| --- | --- | --- | --- | --- | --- | --- |
| 5 | 20 | 1.0 | + | − | 0.595 | 28.7 |
| 6 | 20 | 1.5 | + | − | 0.591 | 29.1 |

[a]Control: Sample processed under standard conditions for cheddar cheese.
[2]Defined as zero.

These results indicate that use of transglutaminase is an important feature of the processes of the invention. The proportion of whey protein product incorporated into the cheese curd increases essentially monotonically as the amount of transglutaminase added is increased.

We claim:

1. A cheese curd comprising protein products originating from a dairy liquid comprising casein and whey protein, wherein the curd is obtained from the dairy liquid by a process that comprises the sequential steps of:

(i) heating the dairy liquid to a temperature of about 55 to about 90° C. for at least about 2 minutes;
  (ii) cooling the heat treated dairy liquid to a temperature of about 30 to about 65° C.;
  (iii) contacting the cooled dairy liquid with a transglutaminase to provide a modified dairy liquid;
  (iv) contacting the modified dairy liquid with a non-rennet protease to form cheese curd and whey liquid; and
  (v) separating the cheese curd from the whey liquid.

2. The cheese curd as described in claim 1, wherein the transglutaminase is selected from the group of transglutaminases isolated from a bacterial source, a fungus, a mold, a fish, and a mammal.

3. The cheese curd as described in claim 2 wherein the transglutaminase is isolated from a bacterial source.

4. The cheese curd as described in claim 3, wherein the transglutaminase is isolated from the genus Streptoverticillium.

5. The cheese curd as described in claim 2, wherein the non-rennet protease is a microbial protease, a plant protease, a fish intestinal protease, or an animal protease other than mammalian rennet.

6. The cheese curd as described in claim 2, wherein the non-rennet protease is isolated from *Bacillus licheniformis, Aspergillus sojae* or *Bacillus thermoproteolyticus*.

7. The cheese curd as described in claim 6, wherein the non-rennet protease is isolated from *Bacillus licheniformis*, is a serine protease specific for glutamic acid and aspartic acid residues, and has an apparent molecular weight of about 23,600 Da.

8. The cheese curd as described in claim 1, wherein the dairy liquid is heated to about 65 to about 85° C.

9. The cheese curd as described in claim 2, wherein the dairy liquid is heated to about 65 to about 85° C.

10. The cheese curd as described in claim 1, wherein the cheese curd is further treated to provide a soft, semi-soft, or a hard cheese.

* * * * *